(12) United States Patent
Sarac

(10) Patent No.: US 7,137,947 B2
(45) Date of Patent: Nov. 21, 2006

(54) ENDOVASCULAR PROSTHESIS HAVING A LAYER OF BIOLOGICAL TISSUE

(75) Inventor: Timur Paul Sarac, Orange Village, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 10/409,884

(22) Filed: Apr. 9, 2003

(65) Prior Publication Data

US 2003/0195608 A1    Oct. 16, 2003

Related U.S. Application Data

(62) Division of application No. 09/908,764, filed on Jul. 19, 2001, now Pat. No. 6,579,307.

(51) Int. Cl.
*A61F 2/04* (2006.01)
*A61F 2/06* (2006.01)

(52) U.S. Cl. .................. 600/36; 623/1.13; 623/1.44

(58) Field of Classification Search ...... 623/1.13–1.48, 623/2.13, 900, 915, 916, 926, 925; 606/194; 600/36

See application file for complete search history.

(56) References Cited

U.S. PATENT DOCUMENTS

| | | | |
|---|---|---|---|
| 4,755,593 A * | 7/1988 | Lauren | 530/356 |
| 4,969,896 A | 11/1990 | Shors | |
| 5,192,311 A | 3/1993 | King et al. | |
| 5,344,442 A * | 9/1994 | Deac | 623/2.12 |
| 5,429,144 A | 7/1995 | Wilk | |
| 5,489,297 A * | 2/1996 | Duran | 623/2.13 |
| 5,556,414 A | 9/1996 | Turi | |
| 5,562,727 A | 10/1996 | Turk et al. | |
| 5,667,523 A | 9/1997 | Bynon et al. | |
| 5,693,085 A | 12/1997 | Buirge et al. | |
| 5,749,880 A | 5/1998 | Banas et al. | |
| 5,865,723 A | 2/1999 | Love | |
| 5,876,432 A | 3/1999 | Lau et al. | |
| 5,891,193 A | 4/1999 | Robinson et al. | |
| 6,077,217 A | 6/2000 | Love et al. | |
| 6,187,039 B1 * | 2/2001 | Hiles et al. | 623/1.44 |
| 6,245,100 B1 | 6/2001 | Davila et al. | |
| 6,331,191 B1 | 12/2001 | Chobotov | |

(Continued)

FOREIGN PATENT DOCUMENTS

WO    WO 9709006 A1    3/1997

OTHER PUBLICATIONS

Sarac et al. In vivo and mechanial properties of peritoneum/fascia as a novel arterial substitute. Journal of Vascular Surgery, 2004; 41:490-497.

*Primary Examiner*—David H. Willse
*Assistant Examiner*—Javier G. Blanco
(74) *Attorney, Agent, or Firm*—Tarolli, Sundheim, Covell&Tummino LLP

(57) ABSTRACT

An apparatus (10) for grafting of a blood vessel (12) and a method of forming the apparatus (10) is provided. The apparatus (10) comprises an expandable support member (16) having inner and outer surfaces (36 and 34). The outer surface (34) of the expandable support member (16) is for engaging and adhering to an inside surface (68) of the blood vessel (12). A layer of biological tissue (14) is attached to the inner surface (36) of the support member (16). The layer of biological tissue (14) has an uninterrupted inwardly facing surface (50) for extending confluently with the inside surface (68) of the blood vessel (12) to provide resistance to thrombosis and platelet deposition.

6 Claims, 7 Drawing Sheets

U.S. PATENT DOCUMENTS

| | | |
|---|---|---|
| 6,355,055 B1 | 3/2002 | Waksman et al. |
| 6,358,275 B1 | 3/2002 | McIlroy et al. |
| 6,468,300 B1 | 10/2002 | Freidberg |
| 6,475,232 B1 | 11/2002 | Babbs et al. |
| 2001/0041928 A1 | 11/2001 | Pavcnik et al. |
| 2002/0123789 A1* | 9/2002 | Francis et al. ............ 623/1.13 |
| 2002/0143393 A1 | 10/2002 | Cox |
| 2003/0023303 A1 | 1/2003 | Palmaz et al. |
| 2003/0075170 A1 | 4/2003 | Deem et al. |
| 2003/0195608 A1 | 10/2003 | Sarac |
| 2004/0093070 A1 | 5/2004 | Hojeibane et al. |

* cited by examiner

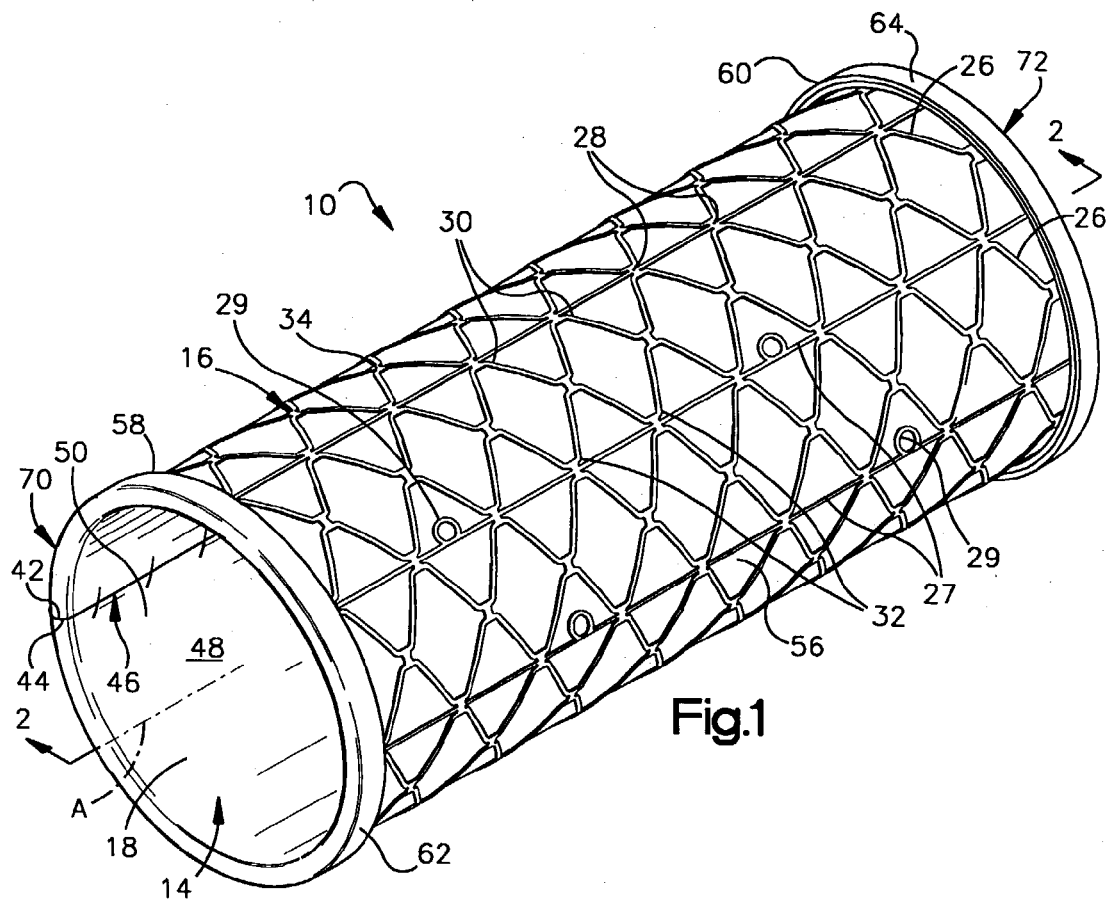
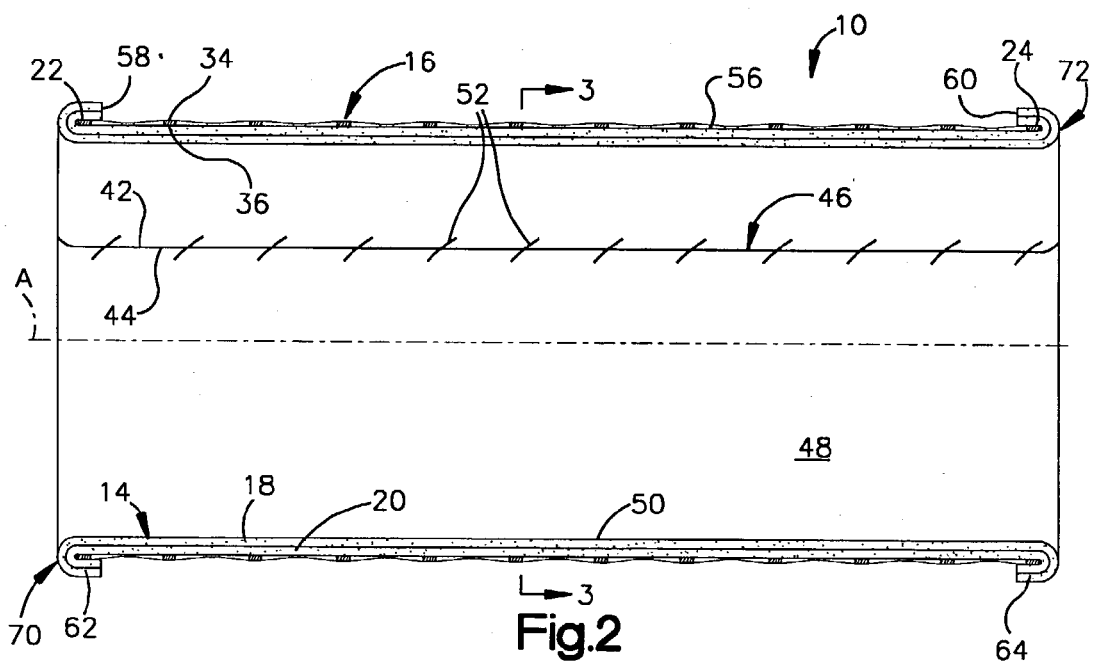

ENDOVASCULAR PROSTHESIS HAVING A LAYER OF BIOLOGICAL TISSUE

CROSS-REFERENCE TO RELATED APPLICATIONS

This application is a divisional of U.S. patent application Ser. No. 09/908,764, filed Jul. 19, 2001, now U.S. Pat. No. 6,579,307 B2, which is assigned to the assignee of the present application.

TECHNICAL FIELD

The present invention relates to an endovascular prosthesis and to a method of forming the endovascular prosthesis.

BACKGROUND OF THE INVENTION

Surgical procedures in which a cardiovascular prosthesis is implanted into a patient's blood vessel are common in treating many vascular disorders. For example, one common type of cardiovascular prosthesis is an endovascular prosthesis that is used to strengthen a blood vessel wall in the location of an aneurysm, or to open an occlusion in a blood vessel.

A typical endovascular prosthesis includes a flexible, tubular member, made of fabric or PTFE, that may be anchored with sutures or carried by one or more support structures known as stents. Generally, each stent is formed from a material having an elasticity sufficient to permit radial expansion of the stent and having a strength sufficient to prevent radial collapse or burst. Such stents are typically formed from stainless steel, titanium, Nitinol, or a suitable plastic.

A common endeavor in the field of cardiovascular prosthetics is to increase the patency rate of prostheses. Thrombosis and platelet deposition on surfaces of a cardiovascular prosthesis reduce the patency rate of the prosthesis. For example, thrombosis and platelet deposition within an endovascular prosthesis may occlude the conduit defined by the endovascular prosthesis.

Many factors contribute to thrombosis and platelet deposition on the surfaces of known cardiovascular prosthesis. The most common factors are dependent upon the material or materials forming the inner surface of the conduit of the endovascular prosthesis. Typically, thrombosis and platelet deposition begin to occlude the conduit of the endovascular prosthesis when the material or materials forming the conduit of the endovascular prosthesis are foreign to the patient's body. A thrombus begins to form on the inner surface of the conduit of the endovascular prosthesis and extends annularly about the inner surface of the conduit. Eventually, the thrombus can severely restrict blood flow through the conduit defined by the endovascular prosthesis and, if left untreated, can completely occlude the conduit.

Additionally, thrombosis and platelet deposition may occur as a result of irregularities on the inner surface of a cardiovascular prosthesis. The irregularities may be formed by the structure of an inner stent that is used to support the cardiovascular prosthesis, or may be formed by the inner surface of the flexible member used for the prosthesis.

SUMMARY OF THE INVENTION

The present invention is an apparatus for grafting of a blood vessel or other portion of the cardiovascular system. The blood vessel has an inside surface that defines a conduit for directing blood flow. The apparatus comprises an expandable support member having inner and outer surfaces. The outer surface of the expandable support member is for engaging and adhering to the inside surface of the blood vessel. A layer of biological tissue is attached to the inner surface of the support member. The layer of biological tissue has an uninterrupted inwardly facing surface for extending confluently with the inside surface of the blood vessel to provide resistance to thrombosis and platelet deposition as blood flows through the conduit.

According to one aspect of the invention, the layer of biological tissue is selected from the group consisting of peritoneum, pleura, and pericardium.

In a further aspect of the invention, a graft for a blood vessel is provided. The blood vessel has an inside surface that defines a conduit for directing blood flow. The graft comprises a layer of biological tissue having an uninterrupted inwardly facing surface for extending confluently with the inside surface of the blood vessel to provide resistance to thrombosis and platelet deposition as blood flows through the conduit.

According to another aspect of the present invention, the layer of biological tissue comprises an inner lining of a serous membrane that is supported by an outer lining of associated fascia. The outer lining of associated fascia serves as a structural support for the inner lining of serous membrane.

The present invention also provides a method for forming a graft for insertion in a blood vessel. The blood vessel has an inside surface that defines a conduit for directing blood flow. According to the inventive method, an expandable support member having inner and outer surfaces is provided. The outer surface of the support member is for engaging and adhering to the inside surface of the blood vessel. A layer of biological tissue having an uninterrupted inwardly facing surface for extending confluently with the inside surface of the blood vessel to provide resistance to thrombosis and platelet deposition as blood flows through the conduit is also provided. The layer of biological tissue is molded into a desired shape. The layer of biological tissue is attached to the inner surface of the support member.

In yet another aspect of the present invention, a method for preparing a patch for insertion in a blood vessel is provided. The blood vessel has an inside surface that defines a conduit for directing blood flow. According to the method, a layer of biological tissue comprising an inner lining of a serous membrane supported by an outer lining of associated fascia is harvested. The inner lining of serous membrane has an uninterrupted inwardly facing surface for extending confluently with the inside surface of the blood vessel to provide resistance to thrombosis and platelet deposition as blood flows through the conduit. The layer of biological tissue is molded into a desired shape. The layer of biological tissue is packaged in a sterile, biological medium and stored within a vacuum-packed container.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a perspective view of an apparatus constructed in accordance with the present invention;

FIG. 2 is a view along line 2—2 in FIG. 1;

DETAILED DESCRIPTION OF THE INVENTION

Figure 5:
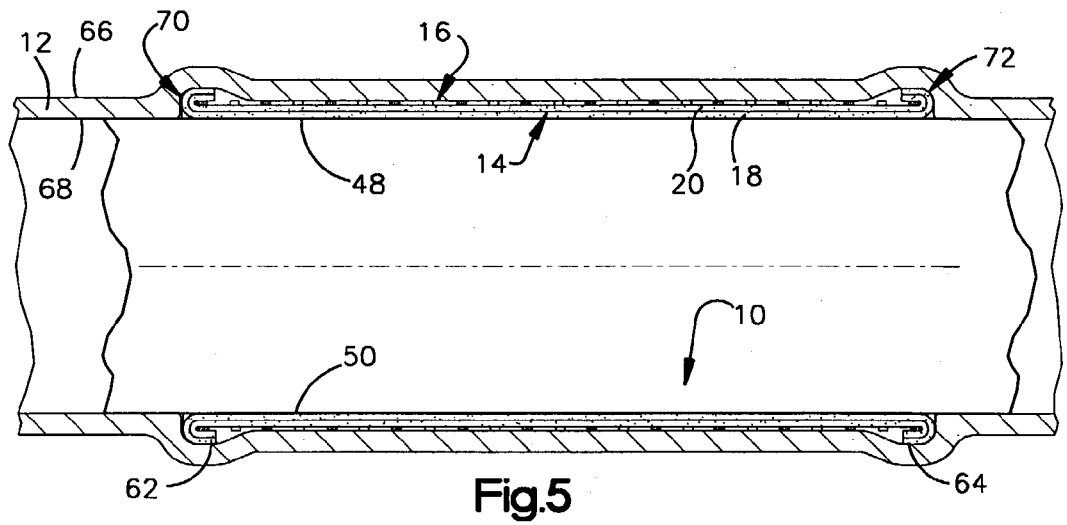
FIG. 5 is a sectional view illustrating the apparatus of FIG. 1 implanted in a blood vessel.

FIG. 1 is a perspective view of an apparatus 10 constructed in accordance with the present invention. The apparatus 10 is a cardiovascular graft for grafting of a blood vessel 12 (FIG. 5). The apparatus 10 includes a layer of biological tissue 14 and an expandable support member 16 or stent.

Figure 3:
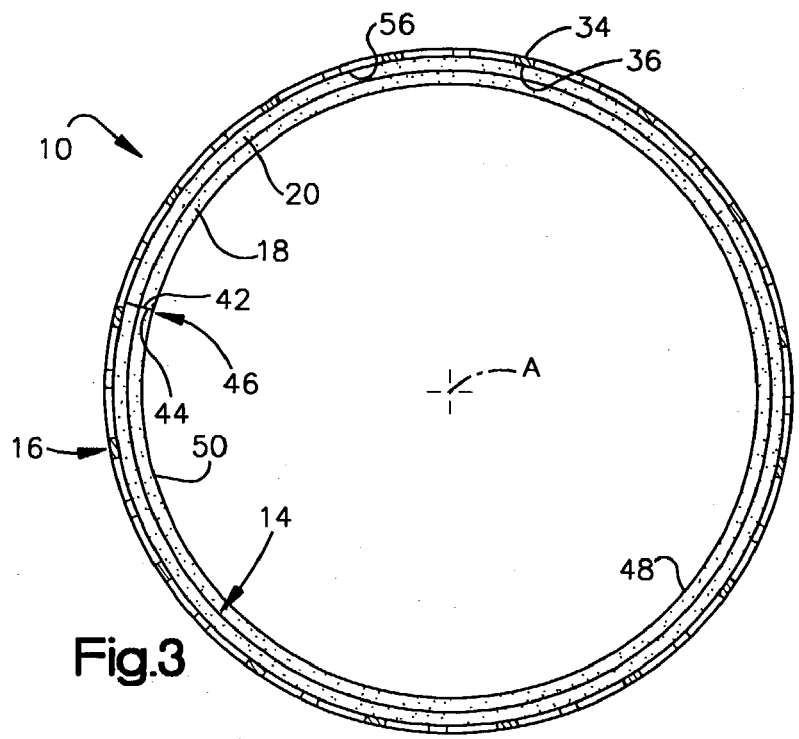
FIG. 3 is a view along line 3—3 in FIG. 2.

The layer of biological tissue 14 includes an inner lining 18 and an outer lining 20 (FIGS. 2 and 3). The inner lining 18 is a serous membrane and the outer lining 20 is fascia associated with the serous membrane. The biological tissue 14 is autogenous tissue. Alternatively, cadaveric tissue or xenogeneic tissue may be used. According to one embodiment, the layer of biological tissue 14 is harvested from the peritoneum. Alternatively, the biological tissue may be harvested from the pericardium or from the pleura. As an alternative to a layer of biological tissue 14, a layer of artificial tissue that mimics the characteristics of peritoneal, pleural, or pericardial membrane may be used. The artificial tissue may be constructed from collagen scaffolding that is seeded with tissue cells, such as human keratinocytes. The artificial tissue may also include a basement membrane. The basement membrane may be a fascia lining or another known artificial lining.

The biological tissue 14 is harvested in sheets of appropriate size. Conventional techniques are used for harvesting the biological tissue 14. The sheet of biological tissue 14 is fixed or preserved with alcohol, glutaraldehyde, and/or another biological solution. After being fixed, the biological tissue 14 is trimmed or cut into the desired shape and size. It is noted that the biological tissue 14 may shrink slightly when fixed. Thus, the biological tissue 14 should be fixed prior to being trimmed to the desired shape and size. Preferably, the biological tissue 14 is trimmed into a rectangular shape. After being trimmed, the biological tissue may be bathed in the biological solution.

The expandable support member 16 is tubular and extends axially from a first end 22 (FIG. 2) to a second end 24. The expandable support member 16 illustrated in FIG. 1 is a mesh structure that includes a plurality of support beams 26 and a plurality of axially extending support rods 27.

Each support beam 26 has a generally sinusoidal shape. The wavelength of each of the support beams 26 is identical or nearly identical to the wavelength of adjacent support beams. Circumferentially adjacent support beams 26 are 180° out of phase from one another. Connector bars 28 (FIG. 1) connect the peaks 30 of each support beam 26 to the associated troughs 32 (FIG. 1) of the adjacent support beam. The amplitude (or height) of each support beam 26 is designed so that a whole number of support beams forms the circumference of the expandable support member 16.

Each of the axially extending support rods 27 extends parallel to axis A. The support rods 27 add additional support to the expandable support member 16. One embodiment of the apparatus 10 includes eight support rods 27 that are equally spaced about the circumference of the expandable support member 16. In the embodiment illustrated in FIG. 1, two support beams 26 are located between adjacent support rods 27.

The expandable support member 16 also includes a plurality of eyelets 29, four of which are shown in FIG. 1. Each eyelet 29 extends from one of the support rods 27. The eyelets 29 illustrated in FIG. 1 are circular, however other shapes may be used. The eyelets 29 provide a means for suturing the layer of biological tissue 14 to the outer support member 16.

The expandable support member 16 is formed from an expandable metal, such as Nitinol. Alternatively, the expandable support may be formed from a fabric layer such as Dacron® or a plastic material such as polytetraflouroethylene (PTFE).

The expandable support member 16 includes an outer surface 34 and an inner surface 36 (FIG. 2). The outer surface 34 is generally cylindrical and extends axially along axis A. The inner surface 36 is also generally cylindrical and is coaxial with the outer surface 34.

Alternatively, the expandable support member 16 may include any known stent structure that is expandable and that defines inner and outer surfaces 36 and 34, respectively. Although the apparatus 10 is illustrated as being cylindrical with a circular cross-sectional shape, the cross-sectional shape of the apparatus may alternatively be elliptical, polygonal, or cone-shaped.

Figures 4A, 4B:
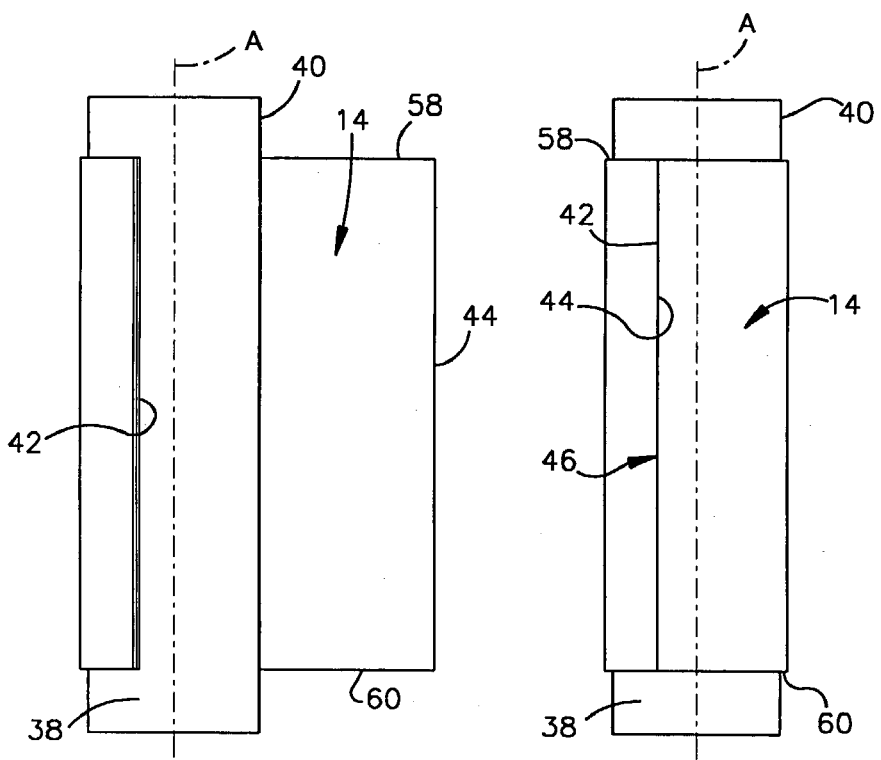
FIGS. 4a–4f illustrate the method of forming the apparatus of FIG. 1.

FIGS. 4a–4f illustrate a method for forming the apparatus 10 of the present invention. The method begins at FIG. 4a with a dowel 38 and a sheet of biological tissue 14 that has been fixed and trimmed into a rectangular shape. The dowel 38 is formed from glass. The dowel 38 illustrated in FIG. 4a is cylindrical and has an outer surface 40 with a circular cross-sectional shape. Alternatively, the dowel 38 may be cone-shaped. A circumference of the outer surface 40 of the dowel 38 is equal to a width of the biological tissue 14. The width of the biological tissue 14 is defined as the distance between a first side surface 42 and a second side surface 44. FIG. 4a illustrates the biological tissue 14 being wrapped or rolled around the dowel 38.

FIG. 4b illustrates the biological tissue 14 completely wrapped around the dowel 38. When completely wrapped around the dowel 38, the first side surface 42 of the biological tissue 14 abuts, rather than overlaps, the second side surface 44 of the biological tissue 14. An axially extending seam 46 is defined at the location where the first side surface 42 and the second side surface 44 meet. The seam 46 extends along an axial length of the biological tissue 14. The axial length of the biological tissue 14 is defined as a distance between a first axial end 58 and a second axial end 60.

The first side surface 42 abuts the second side surface 44 such that the inner surface 48 (FIGS. 1–3) of the apparatus 10, which is defined by an inner surface 50 (FIGS. 13) of the inner lining 18 of the biological tissue 14, is smooth, continuous, and uninterrupted. Since the inner surface 48 of the apparatus 10 has no projections or irregularities, such as would be present if the biological tissue 14 were overlapped, thrombosis and platelet deposition at the seam 46 are resisted. An additional benefit of abutting the first and second side surfaces 42 and 44 of the biological tissue 14 together is that the smooth, continuous, and uninterrupted inner surface 48 of the apparatus 10 does not create turbulent flow through the apparatus.

Figure 4C:
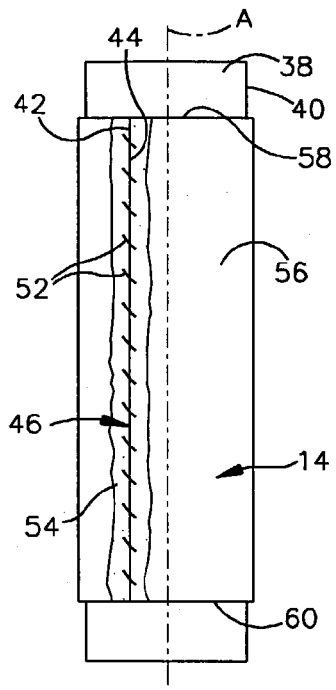

In FIG. 4c, the first side surface 42 of the biological tissue 14 is attached to the second side surface 44 of the biological tissue 14 using sutures 52. The sutures 52 extend radially inwardly through the biological tissue 14 and generally circumferentially between areas adjacent the first and second side surfaces 42 and 44. The biological tissue 14 remains on the dowel 38 while the sutures 52 are sewn in place. A layer of biological glue 54 may be placed over the seam 46 on an outer surface 56 of the biological tissue 14. The biological glue 54 helps to ensure that the inner surface 48 of the apparatus 10 remains smooth, continuous, and uninterrupted. The biological glue 54 also aids in completely sealing the seam 46 to prevent any leakage through the seam 46.

Figure 4D:
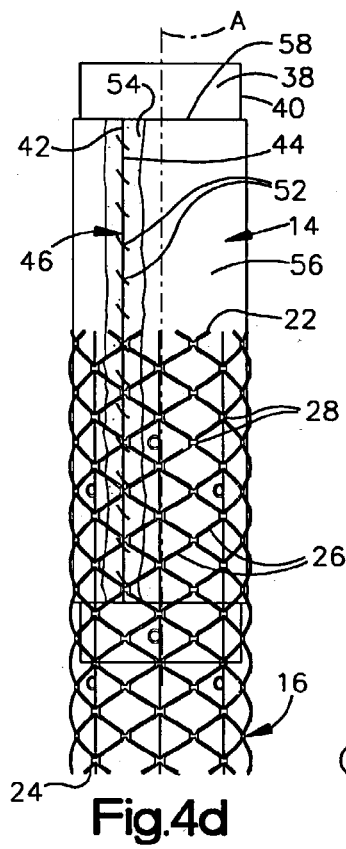

FIG. 4d illustrates the expandable support member 16 being placed over the biological tissue 14. The expandable support member 16 forms an outer support for the biological tissue 14. The expandable support member 16 forms the radially outermost component of the apparatus 10. The radially innermost component of the apparatus 10 is formed by the serous membrane lining 18 of the layer of biological tissue 14.

To place the expandable support member 16 over the biological tissue 14, the expandable support member 16 is expanded. Any known method for expanding the expandable support member 16 may be used, such as heating or balloon dilation of the expandable support member. The dowel 38 and the biological tissue 14 that is being held on the dowel 38 are inserted into the first end 22 of the expandable support member 16, as shown in FIG. 4d. The expandable support member 16 and the dowel 38 are moved relative to one another until an equivalent amount of biological tissue 14 extends axially outwardly of both the first and second ends 22 and 24 of the expandable support member 16.

The expandable support member 16 is then constricted until the inner surface 36 of the expandable support member 16 engages the outer surface 56 of the biological tissue 14 equally about the circumference of the outer surface 56 of the biological tissue 14. Next, the biological tissue 14 is attached to the expandable support member 16. Preferably, sutures (not shown) are used to attach the biological tissue 14 to the expandable support member 16. Each suture extends through the biological tissue 14 and a portion of the suture is threaded through one of the eyelets 29 of the expandable support member 16. The suture is then tied outside of the expandable support member 16 and around the respective eyelet 29. The suture holds the biological tissue 14 to the inner surface 36 of the expandable support member 16. The sutures are sufficiently small so that turbulent flow will not result from the interaction of blood flow with the sutures. Alternately, the outer surface 56 of the biological tissue 14 may be glued to the inner surface 36 of the expandable support member 16 using biological glue. When biological glue is used to attach the biological tissue 14 to the expandable support member 16, the support beams 26 and the support rods 27 must have an inner surface area large enough for adhesion of the biological tissue 14.

Figure 4E:
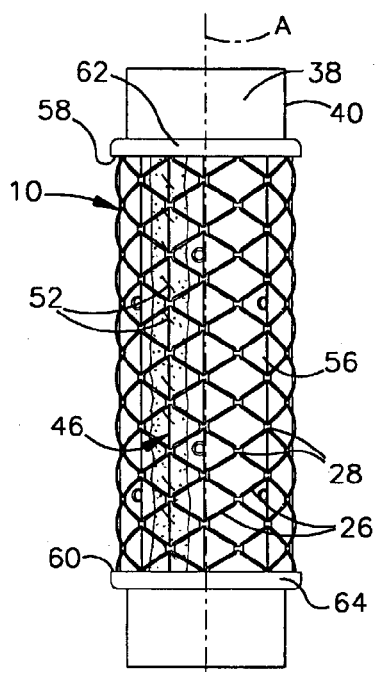

After the biological tissue 14 is attached to the expandable support member 16, the first and second axial ends 58 and 60 of the biological tissue 14 are folded over the first and second ends 22 and 24, respectively, of the expandable support member 16, as is shown in FIG. 4e. The first axial end 58 of the biological tissue 14 is stretched and folded over the first end 22 of the expandable support member 16 to form a first folded portion 62. The first folded portion 62 is then attached to the outer surface 34 of the expandable support member 16 using sutures (not shown). A second axial end 60 of the biological tissue 14 is stretched and folded over the second end 24 of the expandable support member 16 to form a second folded portion 64. The second folded portion 64 is also attached to the expandable support member 16 using sutures (not shown).

Figure 4F:
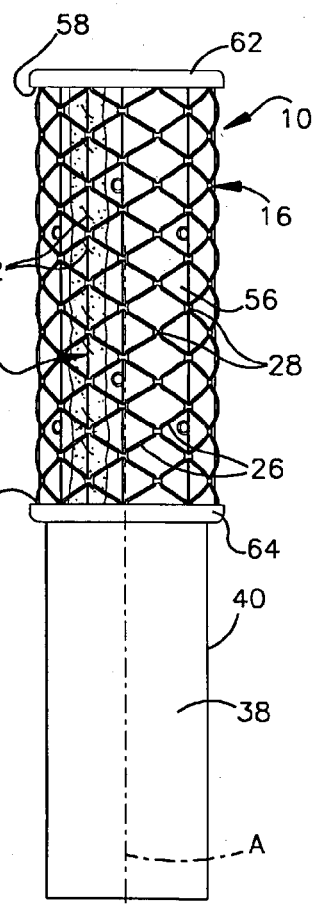

The apparatus 10, including the dowel 38, is stored in a sterile environment until it is time for implantation into a patient. Preferably, the apparatus 10 is submersed in a biological solution and is stored in a sterile, vacuum-packed container (not shown). Alternatively, the dowel 38 may be removed from the apparatus 10 prior to storing the apparatus. FIG. 4f illustrates the dowel 38 being removed from the apparatus 10. Preferably, the dowel 38 and the apparatus 10 are placed in biological or fixing solution to facilitate removal of the dowel 38 from inside the apparatus 10. The solution will sufficiently lubricate the dowel 38 and the biological tissue 14 so that the dowel may be removed from the apparatus 10 without tearing or weakening the biological tissue 14. As a result, the inner surface 48 of the apparatus 10 remains smooth, continuous, and uninterrupted. Alternatively, the apparatus 10 may be expanded and the dowel 38 removed from the expanded apparatus 10.

FIG. 5 illustrates the apparatus 10 of the present invention implanted in a blood vessel 12. The blood vessel 12 includes an outside surface 66 and an inside surface 68. The inside surface 68 of the blood vessel 12 forms a conduit for directing blood flow. The apparatus 10 is delivered and positioned in the blood vessel 12 using methods that are known in the art. Once the apparatus 10 is positioned in the desired location in the blood vessel 12, the expandable support member 16 is expanded, by a balloon (not shown) or through self-expansion as is known in the art. When the expandable support member 16 expands, a first end 70 of the apparatus 10 engages the blood vessel 12 such that an interference fit is created between the first folded portion 62 and the inside surface 68 of the blood vessel 12. Similarly, a second end 72 of the apparatus 10 engages the blood vessel 12 such that an interference fit is created between the second folded portion 64 and the inside surface 68 of the blood vessel 12. An interference fit is also created between the expandable support member 16 and the inner surface 68 of the blood vessel 12 along the axial length of the apparatus 10 that extends between the first and second ends 70 and 72. In addition to the interference fit between the expandable support member 16 and the blood vessel 12, sutures can also used to anchor the expandable support member 16 to the blood vessel 12.

When the apparatus 10 engages and adheres to the inside surface 68 of the blood vessel 12 in the above manner, the inner lining 18 of serous membrane forms the outermost surface at the first and second folded portions 62 and 64. The inner lining 18 bonds to the inside surface 68 of the blood vessel 12 in a normal tissue-healing fashion and prevents the ingrowth of inflammatory tissue. As a result, the bond between the serous membrane of the inner lining 18 at the first and second folded portions 62 and 64 and the inside surface 68 of the blood vessel 12 prevents restenosis or occlusion. Additionally, the healing bond between the serous membrane of the inner lining 18 at the first and second folded portions 62 and 64 and the inside surface 68 of the blood vessel 12 forms more quickly than a bond between the fascia lining 20 and the inside surface 68 of the blood vessel 12.

When implanted in the blood vessel 12, the conduit formed by the inner surface 50 of the biological tissue 14 is confluent with the inside surface 68 of the blood vessel 12. The transition between the inside surface 68 of the blood vessel 12 and the inner surface 50 of the biological tissue 14 is smooth so that thrombosis and platelet deposition is resisted and that blood flow is not restricted when passing through the apparatus 10. The expandable support member 16 provides sufficient support against the internal pressure caused by the blood flow through the apparatus 10, and also resists radial collapse of the blood vessel.

Figure 6:
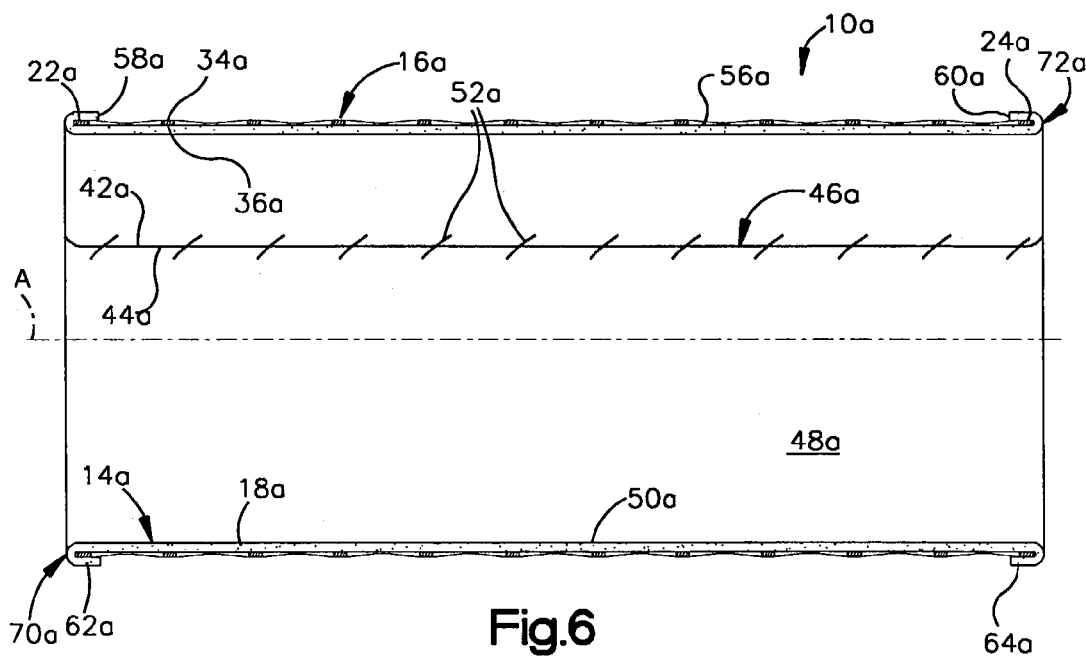
FIG. 6 is a longitudinal sectional view of a second embodiment of an apparatus constructed in accordance with the present invention.

FIG. 6 is a longitudinal sectional view of a second embodiment of an apparatus 10a constructed in accordance with the present invention. Structures of the embodiment shown in FIG. 6 that are similar to structures of FIGS. 1–3 have the same reference numbers with the suffix "a" added. The apparatus 10a is identical to apparatus 10 of FIGS. 1–3 with the exception that the layer of biological tissue 14a in the embodiment of FIG. 6 includes only a layer 18a of serous membrane.

The layer of biological tissue 14a is harvested to include only the layer 18a of serous membrane. The method for harvesting only a layer 18a of serous membrane is known in the art The assembly of apparatus 10a is identical to the assembly of apparatus 10 that is illustrated in FIGS. 4a–4f. When trimmed into the desired shape, the layer of biological tissue 14a includes first and second side surfaces 42a and 44a, respectively, and first and second axial ends 58a and 60a, respectively.

The assembled apparatus includes a seam 46a that is formed from abutting the first and second side surfaces 42a and 44a. The assembled apparatus 10a also includes first and second folded portions 62a and 64a. The first folded portion 62a is formed by folding the first axial end 58a of the layer of biological tissue 14a over the first end 22a of the expandable support member 16a. The second folded portion 64a is formed by folding the second axial end 60a of the layer of biological tissue 14a over the second end 24a of the expandable support member 16a.

The inner surface 48a of the assembled apparatus 10a is defined by the inner surface 50a of the layer 18a of serous membrane. The inner surface 148a of the apparatus 10a is smooth, continuous, and uninterrupted. The smooth, continuous, and uninterrupted inner surface 48a of the apparatus 10a resists thrombosis and platelet deposition.

Figure 7:
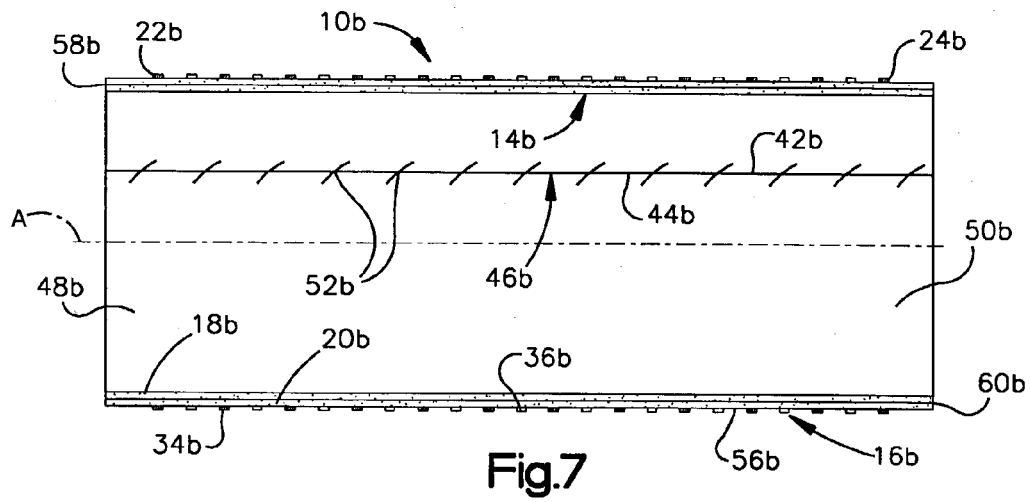
FIG. 7 is a longitudinal sectional view of a third embodiment of an apparatus constructed in accordance with the present invention.

FIG. 7 is a longitudinal sectional view of an apparatus 10b constructed in accordance with a third embodiment of the present invention. Structures of the embodiment shown in FIG. 7 that are similar to structures of FIGS. 1–3 have the same reference numbers with the suffix "b" added.

The apparatus 10b illustrated in FIG. 7 includes a layer of biological tissue 14b and an expandable support member 16b. The layer of biological tissue 14b includes a serous membrane lining 18b and associated fascia lining 20b. The expandable support member 16b has a structure similar to that illustrated in FIG. 1. The layer of biological tissue 14b forms the innermost component of the apparatus 10b.

The layer is biological tissue 14b is formed into a tubular portion by abutting first and second side surfaces 42b and 44b of the biological tissue 14b at a seam 46b. Preferably, the first and second side surfaces 42b and 44b are sutured together at the seam 46b and biological glue (not shown) is applied to an outer surface 56b of the biological tissue 14b.

The outer surface 56b of the layer of biological tissue 14b is attached to the inner surface 36b of the expandable support member 16b. The expandable support member 16b is placed over the biological tissue 14b such that equal amounts of biological tissue 14b extend from the first and second ends 22b and 24b of the expandable support member 16b. Instead of folding the first and second axial ends 58b and 60b of the biological tissue 14b over the expandable support member 16b as discussed above with regard to the embodiment of FIGS. 1–3, the first and second axial ends 58b and 60b of the biological tissue 14b extend axially beyond the first and second ends 22b and 24b of the expandable support member 16b. Thus, in assembling the apparatus 10b, the step illustrated in FIG. 4e is omitted.

When implanted into a blood vessel of a patient, the first and second axial ends 58b and 60b of the tissue 14b engage and are adhered to the inside surface of the blood vessel by the expansion of the expandable support member 16. The extension of the first and second axial ends 58b and 60b of the biological tissue 14b axially beyond the first and second ends 22b and 24b of the expandable support member 16b allows the first and second axial ends of the biological tissue to be sutured directly to the inside surface of the blood vessel.

Figure 8:
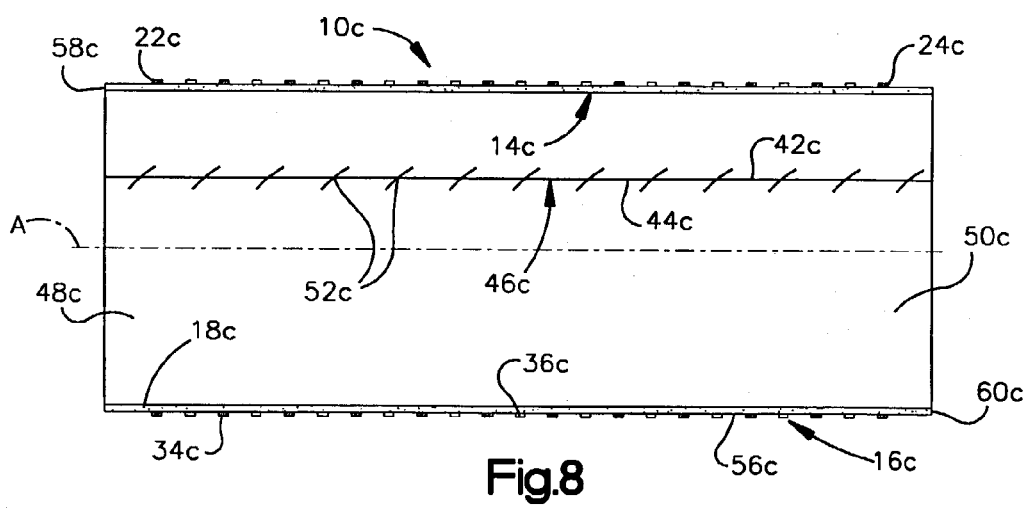
FIG. 8 is a longitudinal sectional view of a fourth embodiment of an apparatus constructed in accordance with the present invention.

FIG. 8 is a longitudinal sectional view of a fourth embodiment of an apparatus 10c constructed in accordance with the present invention. Structures of the embodiment shown in FIG. 8 that are similar to structures of FIG. 7 have the same reference numbers with the suffix "c" replacing the suffix "b". The apparatus 10c is identical to apparatus 10b of FIG. 7 with the exception that the layer of biological tissue 14c in the embodiment of FIG. 8 includes only a layer 18c of serous membrane.

The assembly of apparatus 10c is identical to the assembly of apparatus 10b. When trimmed into the desired shape, the layer of biological tissue 14c includes first and second side surfaces 42c and 44c, respectively, and first and second axial ends 58c and 60c, respectively.

The assembled apparatus includes a seam 46c that is formed from abutting the first and second side surfaces 42c and 44c. The inner surface 48c of the assembled apparatus 10c is defined by the inner surface 50c of the layer 18c of serous membrane. The inner surface 48c of the apparatus 10c is smooth, continuous, and uninterrupted. The smooth, continuous, and uninterrupted inner surface 48c of the apparatus 10c resists thrombosis and platelet deposition.

Figure 9:
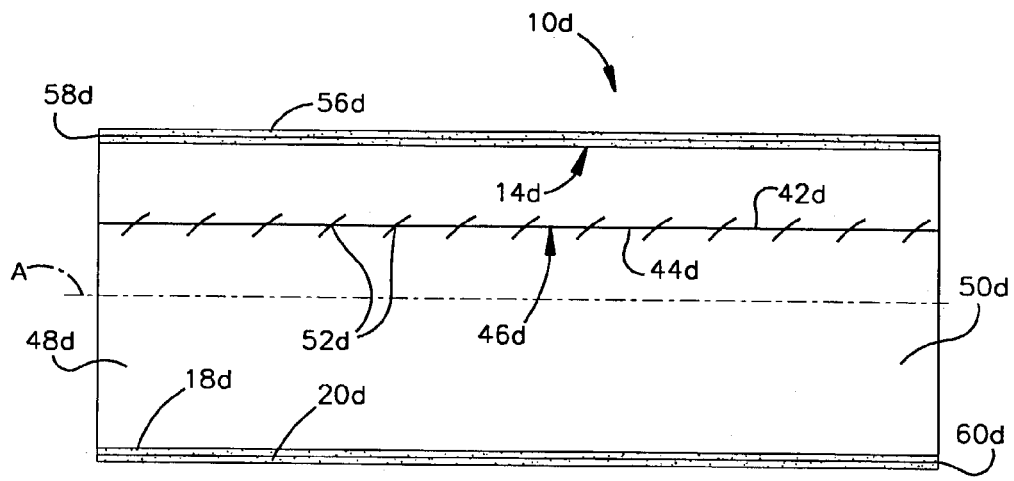
FIG. 9 is a longitudinal sectional view of a fifth embodiment of an apparatus constructed in accordance with the present invention.

FIG. 9 illustrates a longitudinal sectional view of a fifth embodiment of an apparatus 10d constructed in accordance with the present invention. Structures of the embodiment shown in FIG. 9 that are similar to structures of FIG. 7 have the same reference numbers with the suffix "d" replacing the suffix "b".

The apparatus 10d of FIG. 9 is also a cardiovascular graft. The apparatus 10d includes a layer of biological tissue 14d that includes an inner lining 18d of serous membrane and an outer lining 20d of fascia associated with the serous membrane. The layer of biological tissue 14d is rectangular and includes first and second side surfaces 42d and 44d, respectively, and first and second axial ends 58d and 60d, respectively. The inner lining 18d of serous membrane includes an inner surface 50d. The outer lining 20d of fascia includes an outer surface 56d.

The apparatus 10d illustrated in FIG. 9 is cylindrical and is formed by the layer of biological tissue 14d. The first and second side surfaces 42d and 44d of the layer of biological tissue 14d are abutted and secured together to define a seam 46d. Sutures 52d attach the first and second side surfaces 42d and 44d at the seam 46d. A layer of biological glue (not shown) is applied to the outer surface 56d of the outer lining 20d over the seam 46d. The biological glue aids in completely sealing the seam 46d to prevent any leakage through the seam.

To form the apparatus 10d, the steps illustrated in FIGS. 4a to 4c and discussed in detail with regards to apparatus 10 of FIGS. 1–3 are followed. After the step shown in FIG. 4c, the apparatus 10d is stored in a sterile environment until it is time for implantation into a patient. Prior to implantation into the patient, the dowel is removed from the apparatus.

The outer surface 56d of the outer lining 20d forms the outermost component of the apparatus 10d. The inner surface 50d of the inner lining 18d of serous membrane forms the innermost component of the apparatus 10d. The inner surface 50d of the inner lining 18d is smooth, continuous, and uninterrupted. As a result, the inner surface 48d of the apparatus 10d is smooth, continuous, and uninterrupted and resists thrombosis and platelet deposition.

When surgically implanted in a patient, the apparatus 10d is attached using sutures. For example, when used within a blood vessel, the apparatus 10d is sutured to the inside surface of the blood vessel. As a result, the continuous and uninterrupted inner surface 50d of the inner lining 18d is confluent with the inside surface of the blood vessel.

Since the apparatus 10d includes no support structures, the apparatus adapts or conforms to the shape of the blood vessel into which it is attached. Thus, if the inside surface of the blood vessel has an elliptical cross-sectional shape, the apparatus 10d, when attached to the inside surface of the blood vessel, has an elliptical cross-sectional shape.

Figure 10:
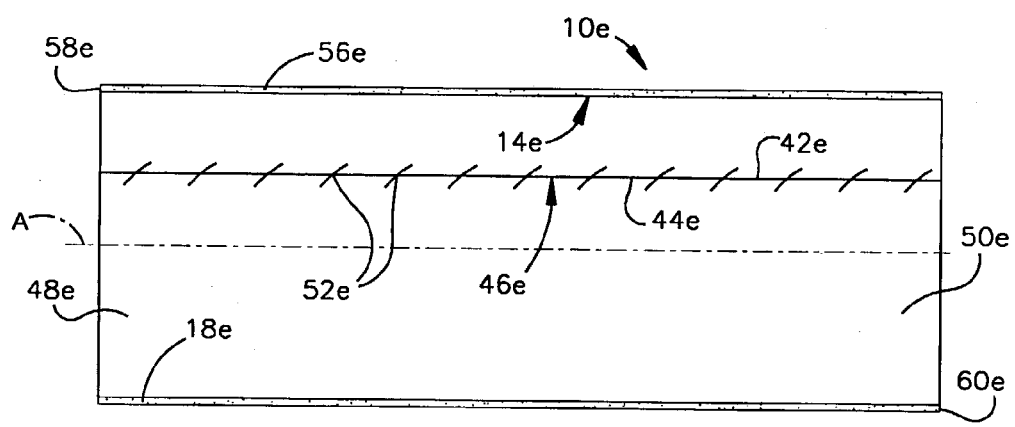
FIG. 10 is a longitudinal sectional view of a sixth embodiment of an apparatus constructed in accordance with the present invention.

FIG. 10 is a longitudinal sectional view of a sixth embodiment of an apparatus 10e constructed in accordance with the present invention. Structures of the embodiment shown in FIG. 10 that are similar to structures of FIG. 9 have the same reference numbers with the suffix "e" replacing the suffix "d". The apparatus 10e is identical to apparatus 10d of FIG. 9 with the exception that the layer of biological tissue 14e in the embodiment of FIG. 10 includes only a layer 18e of serous membrane.

The assembly of apparatus 10e is identical to the assembly of apparatus 10e. When trimmed into the desired shape, the layer of biological tissue 14e includes first and second side surfaces 42e and 44e, respectively, and first and second axial ends 58e and 60e, respectively.

The assembled apparatus includes a seam 46e that is formed from abutting the first and second side surfaces 42e and 44e. The inner surface 48e of the assembled apparatus 10e is defined by the inner surface 50e of the layer 18e of serous membrane. The inner surface 48e of the apparatus 10e is smooth, continuous, and uninterrupted. The smooth, continuous, and uninterrupted inner surface 48e of the apparatus 10e resists thrombosis and platelet deposition.

Figure 11:
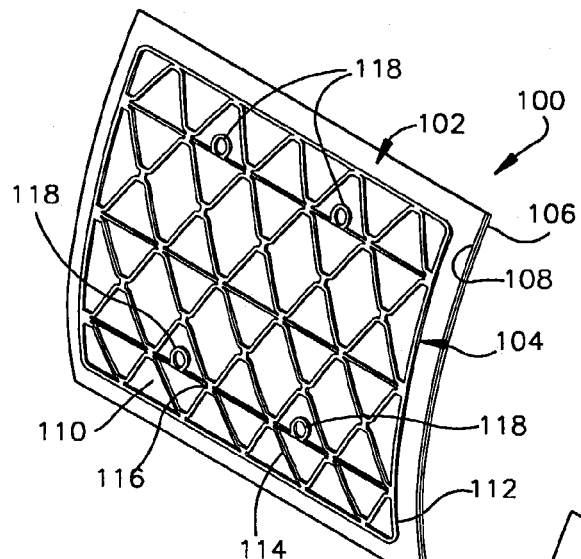
FIG. 11 is a perspective view of a seventh embodiment of an apparatus constructed in accordance with the present invention.

FIG. 11 illustrates a perspective view of a seventh embodiment of an apparatus 100 constructed in accordance with the present invention. The apparatus 100 in FIG. 11 is a patch for repairing a portion of a blood vessel or other membrane within the cardiovascular system of the human body.

The patch 100 includes a layer of biological tissue 102 and an outer support member 104. The layer of biological tissue 102 includes a serous membrane lining 106 and associated fascia lining 108. The serous membrane lining 106 forms an inner surface (not shown) of the biological tissue 102 and the associated fascia 108 forms an outer surface 110 of the biological tissue 102. The layer of biological tissue 102 is illustrated as being rectangular but may be of any desired shape.

The outer support member 104 has the same shape as the biological tissue 102 but is slightly smaller is size. The outer support member 104 may have a curved profile, as is illustrated in FIG. 11, for fitting to a curved surface such as the inside or outside surfaces of a blood vessel.

The outer support member 104 in FIG. 11 is rectangular and includes an outer frame 112 and inner support beams 114. The outer frame 112 defines the shape of the outer support member 104 and provides support near the periphery of the biological tissue 102. The inner support beams 114 of the outer support member 104 provide support for an interior portion of the biological tissue 102. Eyelets 118 are provided through which sutures (not shown) may be threaded when attaching the biological tissue 102 to the outer support member 104.

The outer surface 110 of the biological tissue 102 is attached to the outer support member 104. Preferably, the biological tissue 102 is sutured to the outer support member 104. The peripheral portion of the biological tissue 102 extends outwardly from the outer support member 104. Alternatively, the peripheral portion of the biological tissue 102 may be folded over the outer frame 112 of the outer support member 104.

When implanted in a blood vessel, an outer surface 116 of the outer support member 104 of the patch 100 is placed over an aneurysm or a weakened portion of the blood vessel. The size of the outer support member 104 is preferably larger than the aneurysm or weakened portion of the blood vessel such that the outer frame 112 of the outer support member 104 contacts healthy portions of the inside surface of the blood vessel. The outer periphery of the biological tissue 102 is then attached to the inside surface of the blood vessel, preferably by suturing. The patch 100 may alternatively be placed over the outside surface of the blood vessel or be used on another membrane of the cardiovascular system.

Figure 12:
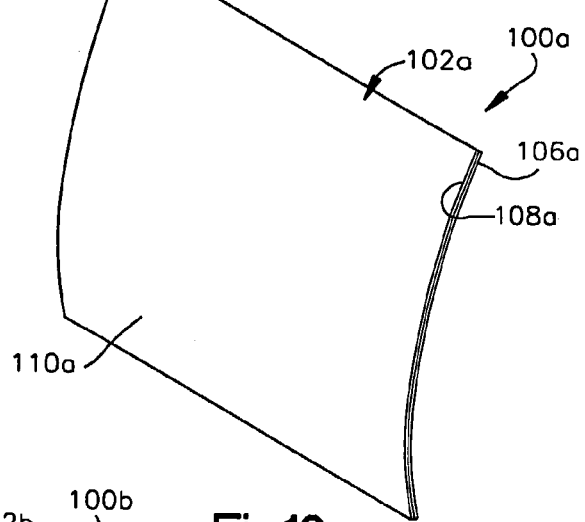
FIG. 12 is a perspective view of an eighth embodiment of an apparatus constructed in accordance with the present invention.

FIG. 12 is a view of an eighth embodiment of an apparatus 100a constructed in accordance with the present invention. Structures of the embodiment shown in FIG. 12 that are similar to structures of FIG. 11 have the same reference numbers with the suffix "a" added.

The apparatus 100a of FIG. 12 is also a patch for repairing a portion of a blood vessel or other membrane within the cardiovascular system of the human body. The patch 100a includes a layer of biological tissue 102a. The patch 100a of FIG. 12 does not include a support structure such as the outer support structure 104 illustrated in FIG. 11.

The layer of biological tissue 102a includes a serous membrane lining 106a and associated fascia lining 108a. The serous membrane lining 106a forms an inner surface (not shown) of the biological tissue 102a and the associated fascia 108a forms an outer surface 110a of the biological tissue 102a. The inner surface of the biological tissue 102a is smooth, continuous, and uninterrupted. The layer of biological tissue 102*a* is illustrated as being rectangular but may be of any desired shape.

When implanted in a blood vessel, an outer surface 110*a* of the associated fascia 108*a* of the layer of biological tissue 102*a* is placed over an aneurysm or a weakened portion of the blood vessel. The biological tissue 102*a* is then attached to the inside surface of the blood vessel, preferably by suturing. Since the patch 100*a* does not include structural support, the patch 100*a* easily adapts to the shape of the blood vessel or membrane to which it is attached to ensure a sufficient area of contact between patch 100*a* and the blood vessel or membrane. The patch 100*a* may alternatively be placed over the outside surface of the blood vessel or be used on another membrane of the cardiovascular system.

Figure 13:
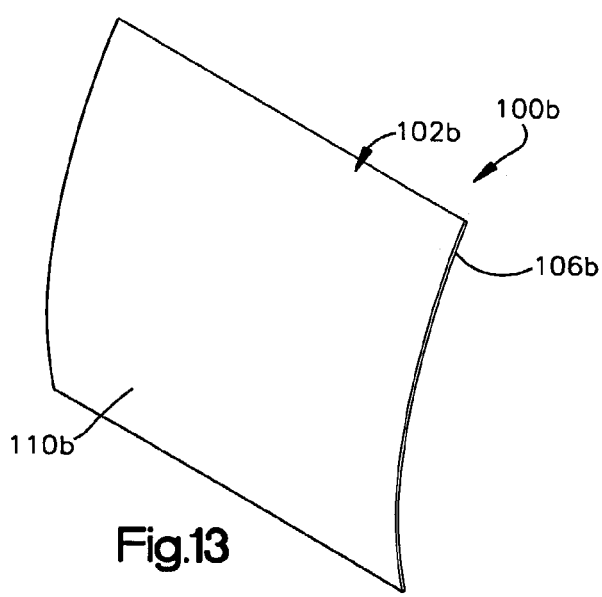
FIG. 13 is a perspective view of a ninth embodiment of an apparatus constructed in accordance with the present invention.

FIG. 13 is a perspective view of a ninth embodiment of an apparatus 100*b* constructed in accordance with the present invention. Structures of the embodiment shown in FIG. 13 that are similar to structures of FIG. 12 have the same reference numbers with the suffix "b" replacing the suffix "a". The apparatus 100*b* is identical to apparatus 100*a* of FIG. 12 with the exception that the layer of biological tissue 102*b* in the embodiment of FIG. 13 includes only a layer 106*b* of serous membrane.

The outer surface 110*b* of the biological tissue 102*b* is formed by an outer surface of the layer 106*b* of serous membrane. The inner surface (not shown) of the biological tissue is formed by an inner surface of the layer 106*b* of serous membrane and is smooth, continuous and uninterrupted.

From the above description of the invention, those skilled in the art will perceive improvements, changes and modifications. For example, a layer of artificial tissue, which mimics the characteristics of the layer of biological tissue, may be used in any of the embodiments discussed above. Such improvements, changes and modifications within the skill of the art are intended to be covered by the appended claims.

Having described the invention, I claim the following:

1. A method for forming a graft for insertion in a blood vessel, the blood vessel having an inside surface that at least partially defines a conduit for directing blood flow, said method comprising the steps of:

providing an expandable support member having a mesh-like structure with inner and outer surfaces, the outer surface for engaging and adhering to the inside surface of the blood vessel;

harvesting a layer of peritoneal tissue comprising an inner lining of a serous membrane having an uninterrupted inwardly facing surface for extending confluently with the inside surface of the blood vessel to provide resistance to thrombosis and platelet deposition as blood flows through the conduit;

forming the layer of peritoneal tissue into a desired shape; and attaching the layer of peritoneal tissue to the inner surface of the support member.

2. The method of claim 1 wherein said step of harvesting a layer of peritoneal tissue comprises harvesting a layer further having an outer lining of associated fascia.

3. The method of claim 1 further comprising the steps of:

fixing the layer of peritoneal tissue with a fixing agent; and trimming the layer of peritoneal tissue.

4. The method of claim 1 wherein said step of forming the layer of peritoneal tissue into a desired shape includes the steps of:

providing a dowel having an outer surface with a cross-section having the desired shape; and wrapping the layer of peritoneal tissue around said outer surface of the dowel.

5. The method of claim 4 wherein said step of attaching the layer of peritoneal tissue to the inner surface of the support member further includes the steps of:

inserting the layer of peritoneal tissue into the support member; and suturing the layer of peritoneal tissue to the support member.

6. The method of claim 5 wherein said step of inserting the layer of peritoneal tissue into the support member includes the steps of:

expanding the support member;

moving the support member relative to the layer of peritoneal tissue until an equal amount of peritoneal tissue extends from oppositely disposed first and second ends of the support member; and constricting the support member around the layer of peritoneal tissue.

* * * * *